United States Patent [19]

Epp

[11] Plant 4,443

[45] Jul. 24, 1979

[54] AFRICAN VIOLET NAMED BRILLIANT EVA

[75] Inventor: Maxiemillian J. Epp, Huttonville, Canada

[73] Assignee: Pan-American Plant Company, West Chicago, Ill.

[21] Appl. No.: 938,116

[22] Filed: Aug. 30, 1978

[51] Int. Cl.[2] ..... A01H 5/00

[52] U.S. Cl. ..... Plt./69

[58] Field of Search ..... Plt./69

*Primary Examiner*—Robert E. Bagwill

*Attorney, Agent, or Firm*—Chas. W. Rummler

[57] ABSTRACT

A new variety of African violet plant distinguished by the medium violet-blue color of its flowers when compared with those of its parent variety, Eva (U.S. Plant Pat. No. 3,611), of which the new plant originated as a sport.

3 Drawing Figures

BACKGROUND OF THE INVENTION

This new variety of African violet plant originated as a sport of the variety Eva (U.S. Plant Pat. No. 3,611) being grown by me in my greenhouses at Huttonville, Ontario, Canada, and was discovered by me in December of 1975. The very pleasant medium blue color of the flowers caused me to reproduce this sport by means of cuttings and asexual propagation of this variety through many successive generations at Huttonville, Ontario, and at West Chicago, Ill., has demonstrated that its distinguishing characteristics hold true from generation to generation and appear to be firmly fixed. Present propagation of this cultivar, by leaf cuttings, is now being done at West Chicago, Ill., and at Parrish, Fla.

DESCRIPTION OF THE DRAWING

My new variety of African violet plant is illustrated by the accompanying drawing which shows the color characteristics and form of its semi-double flowers, the color reproduction being as nearly true as is reasonably possible to be obtained by conventional professional photographic procedures. The flower colors are illustrated by the color patches of RHS91A and 92A.

DESCRIPTION OF THE NEW PLANT

The following is a detailed description of my new African violet cultivar with color designations according to the R.H.S. Colour Chart published by The Royal Horticultural Society of London, England.

THE PLANT

Origin: Sport.

Parentage: Eva (U.S. Plant Pat. No. 3,611).

Classification:

*Botanic.*—*Saintpaulia ionantha.*

*Commercial.*—African Violet.

Form: Compact potted plant.

Height: About 3½ to 4 inches.

Growth: Vigorous, condensed and upright with sturdy and fairly strong stems.

Foliage: The number of leaves varies from plant to plant.

*Size of leaf.*—About 2⅛ inches long and about 2 inches wide for a mature leaf.

*Shape.*—Almost circular with crenate margins having rounded teeth.

*Color.*—Upper side — 137A. Under side — 138D.

*Ribs and veins.*—Pinnately veined and pronounced on the under side.

*Texture.*—Tomentose on both sides.

*Petioles.*—Length — Varies with age of plant. About 2¾ inches long in mature plant.

THE BUD

Form: Spherical, wide bell-shaped when sepals open.

Size: ⅜ inch wide and ¼ inch deep, just before opening.

Opening rate: Very slow — four to five weeks from visible bud until color shows. Then the bud opens into flower within about two weeks.

Color: When sepals divide — 87D.

Sepals: Five, hooded over bud for only a short time after color first shows.

*Form.*—Spear-shaped and upstanding.

*Color.*—Inside and outside — 146D.

Calyx: Splits to star-shape.

*Aspect.*—Inside — smooth; outside — tomentose.

Peduncle: Length — about 1⅜ to 2⅛ inches from base to branching.

*Strength.*—Flexible and fairly erect.

*Color.*—181C.

THE FLOWER

Blooming habit: Recurrent, blooming early, profusely and the year around.

Size of flower: Medium to large.

*Diameter.*—About ⅞ to 1½ inches.

*Depth.*—About ¼ to ½ inch.

Shape of flower: Generally flat, when first opening, with the petaloids held upward, the shape becoming flatter as the flower matures.

Borne: In a cluster of several flowers on one stem, there being several stems on one plant.

Petalage: Five petals, plus several petaloids.

*Arrangement.*—Sympetalous.

*Form.*—Generally circular with irregular but smooth edges.

*Texture.*—Soft. Tomentose on under side.

*Appearance.*—Shiny. Almost glittery.

*Petaloids.*—2 to 7 in number, ⅛ to ⅜ inch in size.

Color: Mature young flower — semi-double.

| Blooming in | February | March |
|---|---|---|
| Face Side: | | |
| Top Petals and Petaloids | 90D, 92A | 91A |
| Lower Petals | 91A, 93D | 91A, 91B |

-continued

| Blooming in | February | March |
|---|---|---|
| Reverse Side: | 88D, 91B | 88D, 91B, 91C |
| Tonality at 8 Feet: | 91A | 91A |

Discoloration: Color fades somewhat after full bloom.

Peduncle: Length — about ¾ to 1⅛ inches.

*Strength.*—Sturdy and upright.

*Color.*—181C.

Effect of weather: Hot weather fades flowers and suppresses flowering. The plant thrives in 80% to 90% humidity.

Persistence: Flowers hang on and dry.

Fragrance: None

Lasting quality: About 14 to 18 days as a fully opened flower.

REPRODUCTIVE ORGANS

Stamens: Some stamens become petaloids.

*Anthers.*—Two in number, each having two cells in basi-fixed arrangement.

*Filament.*—About ⅛ inch long.

*Color.*—Close to 89C.

Pistils: One only.

*Stigma.*—Color — close to 86C.

*Style.*—Up to 5/16 inch long. Color: Close to 92C.

Ovary: Tomentose superior.

This new African violet cultivar is in most respects similar to its parent Eva (U.S. Plant Pat. No. 3,611), differing particularly in the medium violet-blue color of its flowers whereas the parent Eva has flowers of a generally Victoria Violet color like 88A, the flowers of the new plant having a Hyacinth Blue color like 91A.

I claim:

1. A new and distinct cultivar of *Saintpaulia ionantha* substantially as herein shown and described, characterized by its medium violet-blue color when compared with its parent Eva.

* * * * *

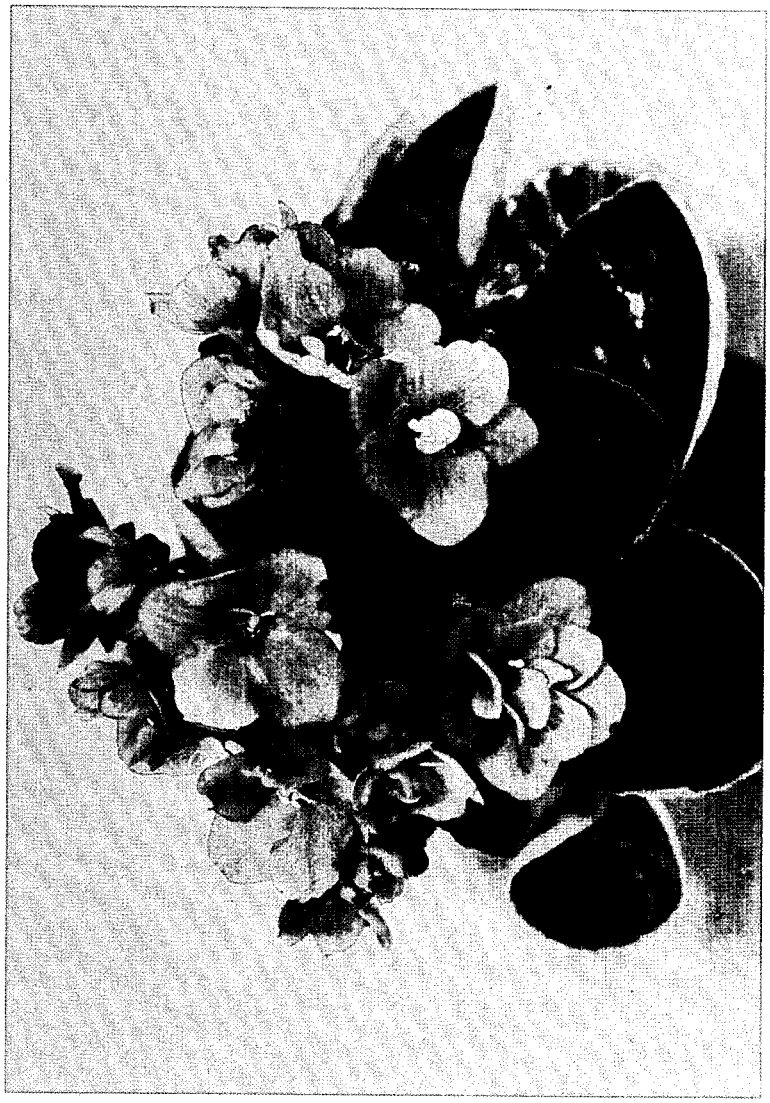
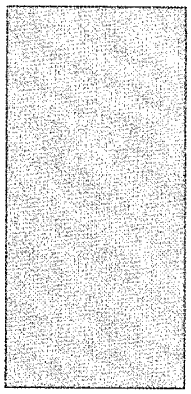
R.H.S. 92 A
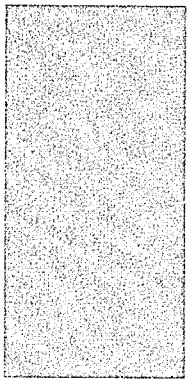
R.H.S. 91A